US00PP20681P2

(12) United States Plant Patent
Giesen

(10) Patent No.: US PP20,681 P2
(45) Date of Patent: Jan. 26, 2010

(54) ***LOBELIA* PLANT NAMED 'TECH DARBULE'**

(50) Latin Name: *Lobelia erinus*
Varietal Denomination: Tech Darbule

(75) Inventor: Eric Giesen, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 12/284,571

(22) Filed: Sep. 23, 2008

(51) Int. Cl.
*A01H 5/00* (2006.01)

(52) U.S. Cl. ..... Plt./451

(58) Field of Classification Search ..... Plt./451
See application file for complete search history.

*Primary Examiner*—June Hwu
(74) *Attorney, Agent, or Firm*—S. Matthew Edwards

(57) ABSTRACT

A new *Lobelia* plant named 'Tech Darbule,' particularly distinguished by medium sized dark blue flowers with small white and darker blue markings, dark green foliage, lanceolate or oblanceolate leaves, freely branching and tight, semi-upright to slightly trailing plant habit, relatively compact and small to medium in size.

1 Drawing Sheet

Latin name of the genus and species of the plant claimed: *Lobelia erinus.*

Varietal denomination: 'Tech Darbule'.

BACKGROUND OF THE NEW PLANT

The present invention comprises a new and distinct cultivar of *Lobelia*, botanically known as *Lobelia erinus* and hereinafter referred to by the cultivar name 'Tech Darbule.'

'Tech Darbule' is a product of a planned breeding program. The new cultivar originated from a hybridization made in January 2004 in Andijk, Netherlands.

The female parent was an unpatented proprietary *Lobelia* plant designated 'LOB04-314-1.' 'LOB04-314-1' has a deeper dark blue flower color and shorter stems than 'Tech Darbule.'

The male parent of 'Tech Darbule' was an unpatented proprietary *Lobelia* plant designated 'LOB04-288-1.' 'LOB04-288-1' has a light blue flower color and more upright plant habit than 'Tech Darbule.'

The resulting seeds were sown in March 2004 and 'Tech Darbule' was selected as one flowering plant within the progeny of the stated cross in July 2004 in a controlled environment in Andijk, Netherlands.

The first act of asexual reproduction of 'Tech Darbule' was accomplished when vegetative cuttings were propagated from the initial selection in the fall of 2004 in a controlled environment in Andijk, Netherlands.

Horticultural examination of plants grown from cuttings of the plant initiated in the spring of 2005 in Andijk, Netherlands, and in Hillscheid, Germany, and continuing thereafter, has demonstrated that the combination of characteristics as herein disclosed for 'Tech Darbule' are firmly fixed and are retained through successive generations of asexual reproduction.

'Tech Darbule' has not been observed under all possible environmental conditions. The phenotype may vary significantly with variations in environment such as temperature, light intensity and day length.

A Plant Breeders' Right for this cultivar was applied for with the European Union on Sep. 13, 2007. 'Tech Darbule' has not been made publicly available more than one year prior to the filing of this application.

DESCRIPTION OF THE DRAWINGS

This new *Lobelia* plant is illustrated by the accompanying photographs which show blooms, buds, and foliage of the plant in full color. The colors shown are as true as can be reasonably obtained by conventional photographic procedures.

DETAILED BOTANICAL DESCRIPTION

Figure 1:
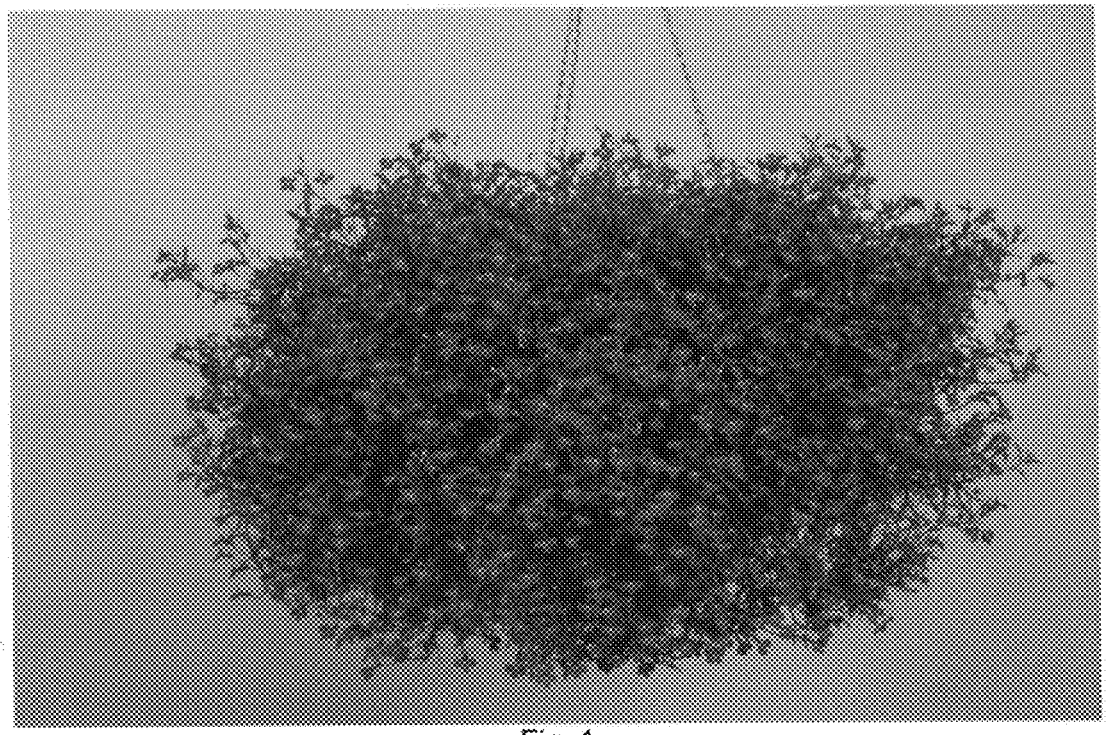
FIG. 1 shows a hanging basket holding 3 plants about 6 months old. The picture was taken in early September 2006.
Figure 2:
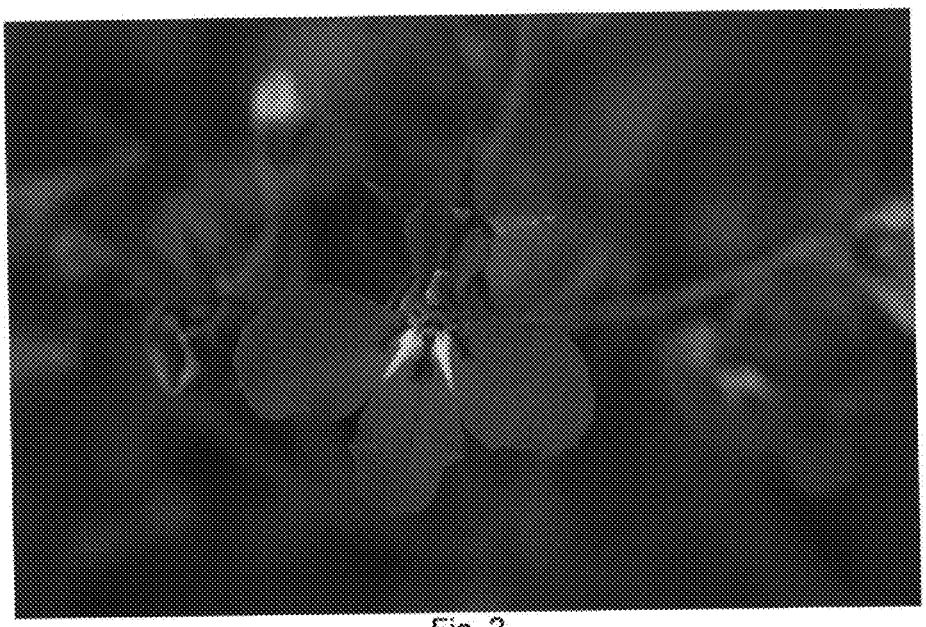
FIG. 2 is a close view of a single flower.

The measurements were taken in Hillscheid, Germany, mainly on May 5, 2007, using 15 week old plants that were growing in 12 cm pots in a greenhouse under relatively cool conditions. Culture of these plants had started in early March 2007 with planting of rooted cuttings that had been pinched once.

Color chart used: The Royal Horticultural Society Colour Chart (R.H.S.), 2001.

BRIEF SUMMARY OF INVENTION

The following observations, measurements, and comparisons describe plants grown indoors and outdoors in Andijk, Netherlands, and in Hillscheid, Germany. The following traits have been repeatedly observed and are determined to be basic characteristics of the new variety. The combination of these characteristics distinguishes this *Lobelia* as a new and distinct variety:

1. Medium sized, deep blue flowers with small white eyes
2. Dark green foliage
3. Well branched and tight, relatively compact growth habit
4. Small to medium sized, mounding to semi-trailing habit

COMPARISON WITH COMMERCIAL CULTIVARS

'Tech Darbule' differs from the commercial cultivar 'Techno Blue' (registered 'Lob Bule,' U.S. Plant Pat. No.

17,250) in that 'Tech Darbule' has a darker blue flower color than 'Lob Bule.' Additionally, the plant habit of 'Tech Darbule' is initially more upright.

Compared with 'Big Blue' (registered 'Weslobigblue,' U.S. Plant Pat. No. 12,634), 'Tech Darbule' has smaller flowers and darker blue color. 'Tech Darbule' also has a more compact habit with shorter internodes than 'Big Blue.'

Plant:

*Growth and habit.*—Vigorous growth habit; dense and freely branched with medium internodes.

*Form.*—Low mounding and semi-trailing.

*Height above soil.*—15–20 cm.

*Plant diameter.*—40–45 cm.

*Number of branches.*—About 50.

*Spread (including flowers).*—Approximately 25 cm, from the base of the main stem to the tips of the branches.

*Spread at the end of the summer.*—55 cm.

*Time to produce a finished flowering plant.*—About 10–12 weeks for a 12 cm pot.

*Outdoor plant performance.*—For hanging baskets, window baskets, in mixed container plantings, or in garden beds.

*Time to initiate and develop roots.*—24 days at 20–24° C.

*Root description.*—Fibrous and freely branching.

Stem:

*Characteristics.*—Quadrangular.

*Stem length.*—20–25 cm.

*Diameter.*—2–3 mm.

*Internode length.*—0.5–1.5 cm.

*Color.*—Deep green, RHS 137A, in parts with anthocyanin: RHS 187A.

*Texture.*—Short hair, hirtellous.

Foliage:

*Arrangement.*—Alternate.

*Shape.*—Oblanceolate to lanceolate, on flowering stems usually narrow lanceolate, sessile without any distinct petiole.

*Apex.*—Acute.

*Base.*—Attenuate to acute.

*Margin.*—Crenate.

*Leaf length (on flowering stems).*—3.2–3.5 cm.

*Leaf width.*—0.4–0.6 cm.

*Size of leaves near the base of stems or on non-flowering stems.*—4.2–6.0 cm in length, 2.1–2.5 cm wide.

*Color upper surface.*—Deep green, between RHS 137A and 139A.

*Color lower surface.*—RHS 138A, most often with anthocyanin, RHS 187C, but weak.

*Venation type.*—Pinnate.

*Venation color.*—RHS 137D on the lower side, indistinct on upper side.

*Texture.*—Both surfaces covered with very short hair, and especially along the leaf veins of lower surface and at the edges.

Inflorescence:

*Blooming habit.*—Continuous through the growing season from spring to the fall.

*Begin of flowering.*—About 10 weeks after planting of rooted cuttings in spring.

*Type of inflorescence.*—Single flowers at the upper nodes of the stems, one flower per leaf node.

*Quantity of flowers per stem.*—About 3–5 open flowers, additionally buds.

*Lastingness of individual blooms on the plant.*—5–6 days.

*Fragrance.*—None.

Flower:

*Corolla type and shape.*—Single, zygomorphic; lower part tube- to funnel-shaped, with the petal lobes opening outwards; two small petals directed upright and 3 mainly fused petals forming the lower lip, salver-shaped with 3 lobes.

*Flower diameter, length.*—1.9–2.0 cm.

*Flower width.*—1.8–2.0 cm.

*Corolla tube length.*—0.8 cm.

*Tube width.*—0.3–0.4 cm.

*Color upper surface.*—RHS 95B.

*Markings in the center.*—Dark blue dots, RHS N89B; and small white macules, RHS 155D.

*Color lower surface.*—RHS 96C mainly, and two pale blue to white macules, RHS 97C to RHS N155A, in the center of the lower lip.

*Color of tube.*—RHS 94A-94B.

Petal lobes:

*Apex.*—Upper petals acute; lower petals rounded to weakly mucronulate.

*Base.*—Fused.

*Margin.*—Entire.

*Texture.*—Glabrous.

*Upper lobes, length (from the corolla opening).*—5–6 mm.

*Upper lobes, width.*—2 mm.

*Lower lobe, length (from the corolla opening).*—9–10 mm.

*Lower lobe, width.*—5–7 mm.

Flower bud:

*Shape.*—Oblong.

*Diameter.*—0.3–0.4 cm.

*Length.*—1.0–1.1 cm.

*Color (at tight bud).*—Pale blue-green, RHS 122D, with blue, from RHS 98B to RHS 98C.

Calyx:

*Form and shape.*—5 sepals in a whorl, slanting outwards.

*Sepal color.*—RHS 137A, both surfaces, tips may be infused with purple: to RHS 137B, tips N186C (both surfaces).

*Length.*—5–6 mm.

*Width.*—1 mm.

*Shape of sepal.*—Ligulate.

*Apex.*—Acute, pointed.

*Base.*—Fused.

*Texture.*—Very short hairs along the edges.

Pedicels:

*Color.*—RHS 137B.

*Length.*—2.0–2.5 cm.

*Diameter.*—0.1 cm.

*Texture.*—Covered with very short, dense hair.

Reproductive organs:

Stamens:

*Quantity.*—5.

*Filament, color.*—Blue, RHS 96D.

*Length.*—0.6 cm.

*Diameter.*—0.1 cm.

*Anther color.*—Grey, RHS 202B.

*Pollen amount.*—Little.

*Pollen color.*—RHS 8B.

Pistil:

*Quantity per flower.*—One.

*Length.*—About 1.0 cm.

*Stigma color.*—RHS 86B.

*Style color.*—RHS 145B.

Fruit and seed set: Are developed in late summer mainly.

*Fruit.*—Small capsule, 5 mm in length, 3 mm in diameter.

*Seeds.*—Nearly round to ovate, very small, under 1 mm in diameter, brown in color.

Disease/pest resistance: Disease resistance or susceptibility other than typical for the species has not been observed on this hybrid.

What is claimed is:

1. A new and distinct variety of *Lobelia* plant named 'Tech Darbule,' substantially as illustrated and described herein.

* * * * *